United States Patent
Ichikawa et al.

[11] Patent Number: 6,024,929
[45] Date of Patent: Feb. 15, 2000

[54] FLUORESCENT LAMP WITH A THIN FILM PHOTOCATALYST, AND METHOD OF CREATING THE SAME

[75] Inventors: Shinichi Ichikawa, Mito; Yoshinori Furukawa; Shigeru Azuhata, both of Hitachi, all of Japan

[73] Assignee: Hitachi Ltd., Tokyo, Japan

[21] Appl. No.: 08/914,754

[22] Filed: Aug. 20, 1997

[30] Foreign Application Priority Data

Aug. 22, 1996 [JP] Japan .................................. 8-220992
Feb. 25, 1997 [JP] Japan .................................. 9-040336

[51] Int. Cl.[7] .................................................. B01J 19/12
[52] U.S. Cl. .................. 422/186; 422/186.3; 250/503.1; 313/158
[58] Field of Search ..................... 422/121, 122, 422/186.3, 186; 250/503.1; 313/158

[56] References Cited

U.S. PATENT DOCUMENTS 5,069,885 12/1991 Ritchie ..................................... 422/186
5,650,126 7/1997 Taoda et al. ............................. 422/122

*Primary Examiner*—Daniel J. Jenkins
*Attorney, Agent, or Firm*—Antonelli, Terry, Stout & Kraus, LLP

[57] ABSTRACT

A light-transmissive and transparent film photocatalyst made of one of anatase-type titanium dioxide and alpha iron oxide is formed on an outside surface of a glass tube used for a fluorescent lamp. The thin film photocatalyst is formed so that electrons and holes generated inside the film by light irradiation can easily and rapidly move to the surface of the film and generate various active species at the surface of the film by contacting with the room air, enabling an excellent deodorization effect, bactericidal and fungicidal activity and contamination preventing effect.

27 Claims, 13 Drawing Sheets

| NO.OF PEAK | 2θ (°) | HALF BAND WIDTH | d-VALVE | INTENSITY | RELATIVE INTENSITY |
|---|---|---|---|---|---|
| 1 | 25.350 | 0.421 | 3.5105 | 4530 | 100 |
| 2 | 30.850 | ***** | 2.8960 | 87 | 2 |
| 3 | 37.050 | 0.294 | 2.4244 | 202 | 6 |
| 4 | 37.900 | 0.471 | 2.3720 | 759 | 18 |
| 5 | 38.700 | 0.176 | 2.3248 | 178 | 4 |
| 6 | 44.500 | ***** | 2.0343 | 68 | 2 |
| 7 | 48.150 | 0.471 | 1.8883 | 703 | 16 |
| 8 | 53.950 | 0.471 | 1.6981 | 391 | 10 |
| 9 | 55.150 | 0.529 | 1.6640 | 340 | 8 |
| 10 | 62.800 | 0.294 | 1.4784 | 247 | 6 |
| 11 | 68.950 | 0.176 | 1.3608 | 97 | 4 |
| 12 | 70.450 | 0.294 | 1.3355 | 97 | 4 |
| 13 | 75.250 | 0.176 | 1.2617 | 143 | 4 |
| 14 | 82.850 | 0.176 | 1.1642 | 91 | 2 |
| 15 | 94.450 | ***** | 1.0494 | 45 | 2 |

FLUORESCENT LAMP WITH A THIN FILM PHOTOCATALYST, AND METHOD OF CREATING THE SAME

BACKGROUND OF THE INVENTION

The present invention relates to a fluorescent lamp having a coating of thin film photocatalyst, which lamp is suitable for use in the home, a vehicle, and any space requiring lighting equipment for lighting the space or purifying air in the space, and wherein the cutting off of ultraviolet light radiated from the fluorescent lamp is desired.

Generally, in a closed space which is poorly ventilated, many malodorous substances, bacteria and fungi, or contaminating particulates are accumulated and spread in the air. The concentration of such undesirable substances in the air is in a range of the order of ppb–ppm or less, and the concentration of bacteria and fungi are much lower than that range. However, the undesirable substances, bacteria or fungi can negatively affect the human body, that is, malodorous substances produce uncomfortable feelings to a human being, and various kinds of bacteria and fungi can cause diseases, such as allergies and illnesses. Fat and oily organic substances can adhere to a surface of an object. This can cause the dust particles in the air to adsorb on the surface. Recently, there has been an urgent demand to develop cleaning techniques which are effective for deodorization, sterilization and decontamination of our living environment.

In the field of lighting equipment, techniques for decomposing malodorous substances by using the effects of a photocatalyst provided in lighting equipment have been proposed. For example, a lamp, on a surface of which a titanium oxide film is coated, is disclosed in JP-A-304237/1994 (corresponding to Germany Patent Application Laid-Open DE 4410476 A1).

In the above-mentioned laid-open documents, it is indicated that malodorous substances in air can be decomposed and removed by oxidation and reduction initiated by pairs of an electron and a hole generated in the titanium oxide film on which light is irradiated from the inside of the lamp.

SUMMARY OF THE INVENTION

An object of the present invention is to provide a fluorescent lamp having a coating of a thin film photocatalyst on the outer surface thereof, so as to provide a higher effectiveness in deodorizing, sterilizing and decontaminating than the previously proposed lamp of this type.

Another object of the present invention is to present a method of creating a fluorescent lamp with a thin film photocatalyst to attain the above objectives.

To attain the above objects, the present invention provides a fluorescent lamp including a light transmissive glass tube, a thin film fluorescent substance applied on an inside wall of the glass tube, bases and pins provided at both ends of the glass tube, and mercury and buffer gas enclosed in the glass tube, the fluorescent lamp comprising:

a light transmissive and transparent thin film photocatalyst made of one of titanium oxide having an anatase-type crystal structure, or iron oxide having an alpha-crystal structure $\alpha\text{-}Fe_2O_3$, applied on an outside surface of the glass tube.

Furthermore, the present invention provides a fluorescent lamp including a light transmissive glass tube, a thin film fluorescent substance applied on an inside wall of the glass tube, bases and pins provided at both ends of the glass tube, and mercury and buffer gas enclosed in the glass tube, the fluorescent lamp comprising:

a light transmissive and transparent thin film photocatalyst, made of one of titanium oxide having an anatase-type crystal structure and iron oxide having an alpha-crystal structure, applied on an outside surface of the glass tube, wherein electrons and holes generated in the thin film photocatalyst rapidly move to the surface of the thin film photocatalyst.

In the above-mentioned fluorescent lamp, it is preferable that the thickness of the thin film photocatalyst made of anatase titanium dioxide is in a range of 0.02 $\mu$m to 2 $\mu$m, or that the thickness of the thin film photocatalyst made of alpha iron oxide is in a range of 0.01 $\mu$m to 0.1 $\mu$m m. If the thickness of the photocatalyst is too thin so as to fall below these ranges, the effects of deodorization, sterilization and decontamination can not be sufficiently obtained, and if the thickness is too large so as to fall beyond these ranges, the light transmittance is rather degraded and this results in the loss of function as a lamp.

The fluorescent lamp according to the present invention is different from the fluorescent lamp disclosed in JP-A-304237/1994, in which a titanium oxide film with unspecified crystal structure is coated on a surface of the lamp, in that an anatase-type titanium dioxide is coated on an outside surface of the fluorescent lamp in accordance with the present invention. Although a crystal structure is not disclosed in JP-A-304237/1994, the structure of the titanium oxide film was examined and found to be amorphous and not the anatase-type crystal structure we have in our invention.

Moreover, in the above-mentioned fluorescent lamp of the present invention, it is preferable that the thin film photocatalyst is prepared so that electrons and holes generated within the thin film photocatalyst by light irradiated on the film can rapidly move throughout the film, which is realized by improving the light transmission and transparency of the film. A highly light-transmissive and transparent photocatalyst is obtained, for example, by preparing the film so that the crystal of anatase titanium dioxide or alpha iron oxide are two-dimensionally and continuously structured to form a sheet of thin film. The above-mentioned thin film photocatalyst can be formed by our method based on a sol-gel process.

Also, in the above-mentioned thin film photocatalyst, it is desirable that the film transmits light in a wave length range of 290 nm–1200 nm and transmits more than 90% of its light in a wave length range of 290 nm–750 nm. By using a thin film photocatalyst having the above-mentioned light transmission property, the effects, of deodorization and decontamination, and the bactericidal effects can be realized without degrading the performance of the fluorescent lamp.

Furthermore, the present invention provides a method to produce a fluorescent lamp including a light transmissive glass tube, a thin film fluorescent substance applied on an inside wall of the glass tube, bases and pins provided at both ends of the glass tube, and mercury and buffer gas enclosed in the glass tube, the method comprising the steps of:

adhering a sol solution containing precursors to one of titanium dioxide and iron oxide to an outside surface of the glass tube, whereas on the inside surface of the tube, the thin film fluorescent substance is coated, and drying and baking the sol solution adhered to the outside surface of the glass tube in order to form a light transmissive and transparent thin film photocatalyst made of one of titanium oxide having an anatase-type crystal structure and iron oxide having an alpha-crystal structure on an outside surface of the glass tube.

Here, it is desirable that a sol solution made of a mixture of titanium alkoxide, acid and alcohol is used to form the thin film titanium dioxide, and also that a sol solution made of a mixture of an iron compound, acid and alcohol is used to form the thin film alpha iron oxide.

It is desirable that the temperature for baking the sol solution adhered to the outside wall of the glass tube is in a rang of 450–600° C. in the case of forming thin film anatase-type titanium oxide and is in a range of 560–770° C. in the case of forming an alpha iron oxide. By baking the sol solution at a temperature in the above-mentioned ranges, an anatase-type titanium dioxide thin film and an alpha iron oxide thin film can be formed. On the contrary, if a baking temperature outside the above-mentioned temperature ranges is employed, the above-mentioned crystal structures can be hardly obtained.

By contacting the outside surface of the glass tube to a surface in a pool of the sol solution, and by rotating the glass tube to cause the sol solution to adhere to the outside surface of the glass tube, a uniform and structurally smooth thin film can be formed on the outside surface of the glass tube.

During this coating process, although undesirable droplets of the sol solution are formed on portions of the glass tube when the rotation of the glass tube is stopped and the glass tube is lifted, the droplets can be removed by using water or an alcohol solution, thus resulting in a commercially presentable lamp.

When light is irradiated on the photocatalyst, the photocatalyst is activated, and various kinds of active species are generated. The generated active species initiate chemical reactions which result in deodorization, sterilization and decontamination. The nearer a light source is to the photocatalyst, the stronger will be the light energy intensity per unit area that the photocatalyst receives. Therefore, a shorter distance between the light source and the photocatalyst enables a higher activity of the photocatalyst. In accordance with the present invention, a light-transmissive and transparent thin film photocatalyst is formed on an outside surface of a glass tube inside of which a light source exists. Therefore, although light is irradiated on the thin film photocatalyst from the opposite side of the reaction surface, since the distance between the light source and the photocatalyst is very short, the feeble light energy of the fluorescent lamp is maximally utilized.

The above-mentioned expression "light transmissive" means that light in a wave length range of 290 nm–1200 nm in the natural light spectrum can be transmitted. Therefore, it is necessary that light irradiated on a surface of the thin film photocatalyst can pass through the film and reach the outside front surface of the film. It is needless to say that the glass tube itself is transparent since the above-mentioned lamp is a fluorescent lamp. The word "transparent" means that an object on one side of the thin film photocatalyst is visible from the other side of the film with the naked-eye. A transparent substance should be able to transmit light in a wave length range with of 290 nm–750 nm. A light in this wave length range is light which can be sensed by the naked-eye. Generally, light radiated from a fluorescent lamp has wave lengths within the above-mentioned range.

The photocatalyst is a special catalyst that can initiate chemical reactions at room temperature by absorbing light energy. If light is irradiated on the photocatalyst, electrons are excited from a valence band to a conduction band beyond a band gap characteristic of the photocatalytic material, and a pair consisting of an electron ($e^-$) and a hole ($h^+$) is generated. That is, in the cax of light irradiation, if photons with a larger energy than the energy band gap, that is, a shorter wave length than that corresponding to the band gap energy (the critical wave length) are irradiated on the photocatalyst, the above-mentioned electron excitation occurs. The critical wave length is about 400 nm in the case of anatase-type titanium dioxide, and about 540 nm for alpha iron oxide. The photon generation rate per unit irradiation area and unit time is proportional to the energy intensity of irradiated light having a wave length within the excitation wave length range.

The electrons and holes generated by the photon-excitation produces various kinds of active species at the surface of the photocatalyst. For example, the electrons react with the oxygen from the air and produce active oxygen ($O_2^-$). On the other hand, the holes react with water from the air and produce protons ($H^+$) and oxygen molecules. The above-mentioned two reactions are combined in various subsequent reactions, and active ozone ($O_3^-$), hydroxide ion ($OH^-$), hydroxide radical ($OH.$), a hydrogen peroxide molecule ($H_2O_2$), etc. are produced. Since the generation rate of the above-mentioned active species per unit irradiation area and unit time is proportional to the generation rate of the electrons and holes, that is, the generation rate of photons, the decomposition rate of harmful substances is proportional to the above-mentioned generation rates.

DETAILED DESCRIPTION OF THE EMBODIMENTS

Figure 1:
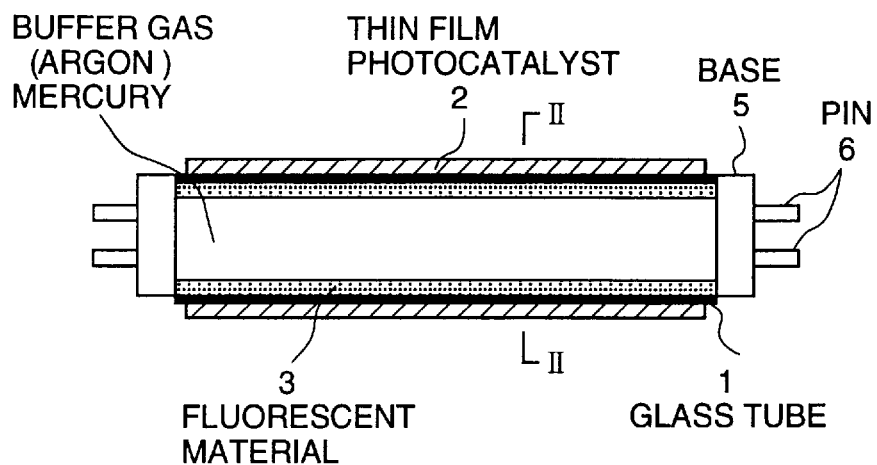
FIG. 1 shows a longitudinal cross-section of a fluorescent lamp representing an embodiment according to the present invention.

Hereinafter, details of the present invention will be explained with reference to the various embodiments shown in the drawings.

Figure 2:
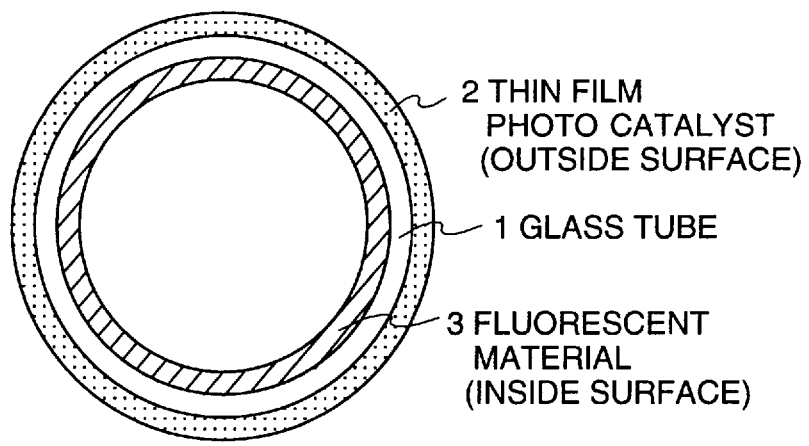
FIG. 2 shows a cross-section of the fluorescent lamp viewed from the position II—II in FIG. 1.

A fluorescent lamp representing an embodiment according to the present invention is shown in FIG. 1 and FIG. 2. FIG. 2 is a cross-section of the fluorescent lamp viewed from the position II—II in FIG. 1. The fluorescent lamp possesses a thin film photocatalyst 2 on an outside surface of a straight tube type glass tube 1. A fluorescent material film 3 is coated on an inside surface of the glass tube 1. In the glass tube 1, a mercury and buffer gas is enclosed. The electric discharge is generated by electrically connecting the lamp to a power source via bases 5 carrying pins 6, and the mercury radiates light in the ultraviolet range. The fluorescent material film 3 receives the radiated ultraviolet light and emits light. As the buffer gas, on inert gas such as neon, argon, krypton, xenon, and so forth, is used.

In the light radiated from a fluorescent lamp, ultraviolet rays in addition to visible light is included. The thin film photocatalyst 2 absorbs the ultraviolet rays radiated from the fluorescent lamp, and other ultraviolet rays irradiated on a surface of the photocatalyst 2, and decomposes malodorous substances, bacteria and fungi or oil substances which are deposited on the surface of the fluorescent lamp, into safe chemicals, such as carbon dioxide, nitrogen and water.

Since the thin film photocatalyst 2 and the thin film fluorescent material 3 are disposed close to each other via the glass plate of the glass tube 1, the energy of the light radiated from the thin film fluorescent material 3 can be efficiently utilized. The shorter the distance between the thin film photocatalyst and the thin film fluorescent material as a light source is, the more light of higher energy intensity will be irradiated on the thin film photocatalyst and the more active species will be generated per unit area of the thin film photocatalyst. In using a feeble light source, such as a fluorescent lamp, the above-mentioned composition of the lamp can more effectively use most of the light radiated from the light source. In the fluorescent lamp of the present invention, the decomposition of harmful substances, such as malodorous substances, is caused by light irradiated on the back surface of the thin film photocatalyst. Consequently, the light which is transmitted through the thin film photocatalyst can further pass to the outside of the fluorescent lamp. By taking advantage of the above-mentioned mechanism of light passing through the thin film photocatalyst, for example, by providing two or more fluorescent lamps neighboring each other, multiple light receptions and excitations can be realized among thin film photocatalysts of plural fluorescent lamps. Thus, a synergistic effect can be realized.

The whole of the thin film photocatalyst is made of anatase-type titanium dioxide or alpha iron oxide, and crystallites composing the whole of the thin film are two-dimensionally and continuously arranged so as to form a thin sheet of the photocatalyst.

A conventional thin film photocatalyst is formed by causing photocatalyst particles to adhere to one another using a binder, and this is distinctly different from the thin film photocatalyst of the present invention, in which no binder is used.

Figure 3:
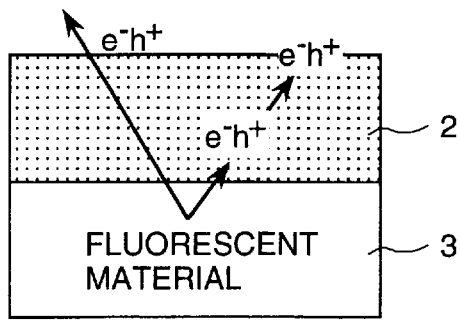
FIG. 3 is a diagram for explaining operations and effects of the fluorescent lamp of the present invention.

The effects of the thin film photocatalyst in which crystallites of anatase-type titanium dioxide or alpha iron oxide are two-dimensionally and continuously arranged will be explained by referring to FIG. 3. At first, the photocatalyst 2 can be excited in the thin film and at a surface of the thin film. When light passes through the thin film photocatalyst, the light excites the photocatalyst and produces pairs, comprising an electron and a hole, in its inside region and at its surface. Then, the produced pairs of an electron and a hole in the inside of the thin film photocatalyst 2 rapidly move to the surface of the thin film. Finally, the pairs of an electron and a hole generate various kinds of active species, and the generated active species chemically decompose harmful substances.

On the other hand, in the case of forming a conventional film photocatalyst with a collection of dispersed particles of photocatalyst, the particles are superimposed on each other in the layer, and a laminated particle layer is formed. Crevices among particle boundaries are also generated. Furthermore, since organic or inorganic binder is used to cause the particles to adhere to each other, the purity of the photocatalyst is deteriorated, and each of distances among the particle becomes larger. Consequently, when light is irradiated on the laminated particle layer, since the light is hardly transmitted into the inner part under the surface of the layer, only the photocatalyst particles at the surface of the layer are excited, and the photocatalyst particles in the inner part of the layer are hardly excited. This problem of the laminated particle layer becomes more severe as the thickness of the layer becomes large. That is, the efficiency of the photocatalytic action is more degraded. Also, electron-hole pairs generated within the particle cannot be transferred to other neighboring particles due to energy barriers at the boundary of the particles. If a binder which is an insulator is used, this problem becomes more severe since the binder cannot transfer electrons. The harmful substances adsorbing to the surface of a layer consisting of photocatalytic particles and binder cannot be chemically reacted when the adsorption site is the binder. This is another disadvantage of a mixture of particles with a binder. On the other hand, in the thin film photocatalyst of the present invention, crystallites of the photocatalyst are tightly connected to each other and are two-dimensionally and continuously arranged, which forms one thin sheet of the photocatalyst. Therefore, light can pass through the film without absorption in other materials and be effectively used. Thus, the efficiency of the photocatalyst is remarkably improved in the thin film photocatalyst of the present invention.

Moreover, in a laminated photocatalyst particle layer, it is preferred to use smaller particles of photocatalyst to increase the surface area of the particles per unit volume. However, since the band gap the of photocatalyst increases by a quantum size effect if the size of a particle is decreased below a critical size, the photocatalyst is excited only by ultraviolet rays of a shorter wave length having higher energy. Therefore, in the case where a photocatalyst is excited by a light source, such as a fluorescent lamp, in which the radiated light has a comparatively low photon energy in the ultraviolet region, or by light ray from the sun, the quantum size effect disadvantageously affects the laminated particle layer type photocatalyst. For titanium dioxide, the critical size of a particle is 10 nm–20 nm. If particles or grains of a smaller size than the critical size are used, although the transparency of the laminated particle layer can be increased, it is not preferable because of the above-mentioned problem of the quantum size effect. Thus, the thin film photocatalyst of the present invention is more advantageous since the quantum size effect does not become a problem.

[Embodiment 1]

In the following, a method of producing, as well as on evaluation of, the physical property of a thin film of titanium dioxide will be explained.

At first, titanium tetra isopropoxide was hydrolyzed by adding a mixture solution of acid and alcohol to a mixture solution of titanium tetra isopropoxide and alcohol, and a titanium sol solution was obtained by processing the obtained titanium hydroxide. The titanium sol solution was coated on a glass substrate of the same composition (soda-lime glass as that of a glass tube typically used in a fluorescent lamp, and the coated substrate was heated to about 500° C. and dried and baked at that temperature. By the sol-gel processing method, condensation polymerization between hydroxyl groups of titanium hydroxide and hydroxyl groups existing at the surface of the glass substrate proceeded, and chemical bonding between titanium dioxide and silicon oxide, which is the dominant component of soda-lime glass, also proceeded. Consequently, a light transmissive and transparent thin film of titanium dioxide was formed on the surface of the glass substrate.

Figure 4:
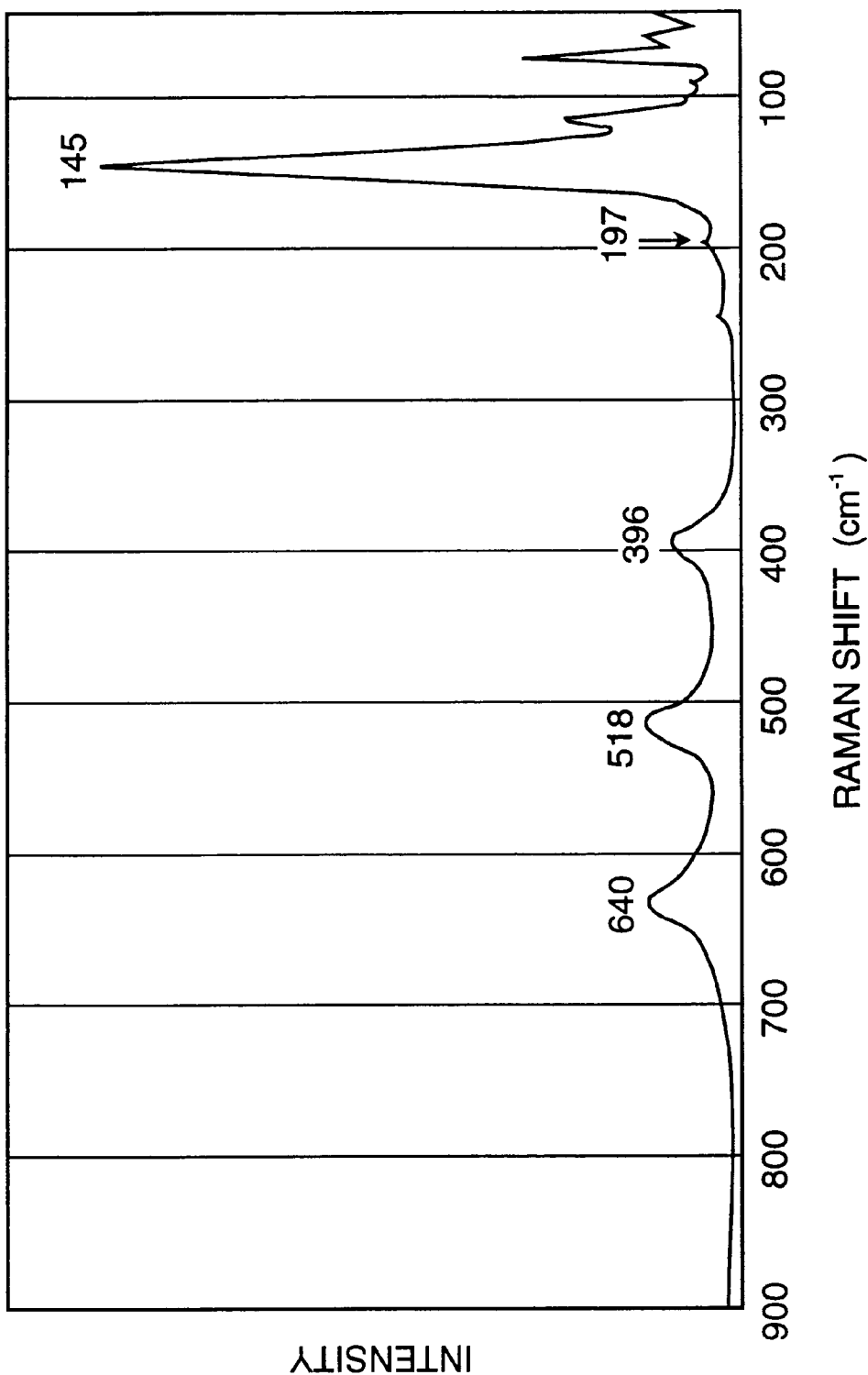
FIG. 4 is a laser Raman spectrum showing the crystal structure of a thin film of titanium oxide applied on a glass substrate.
Figure 5:
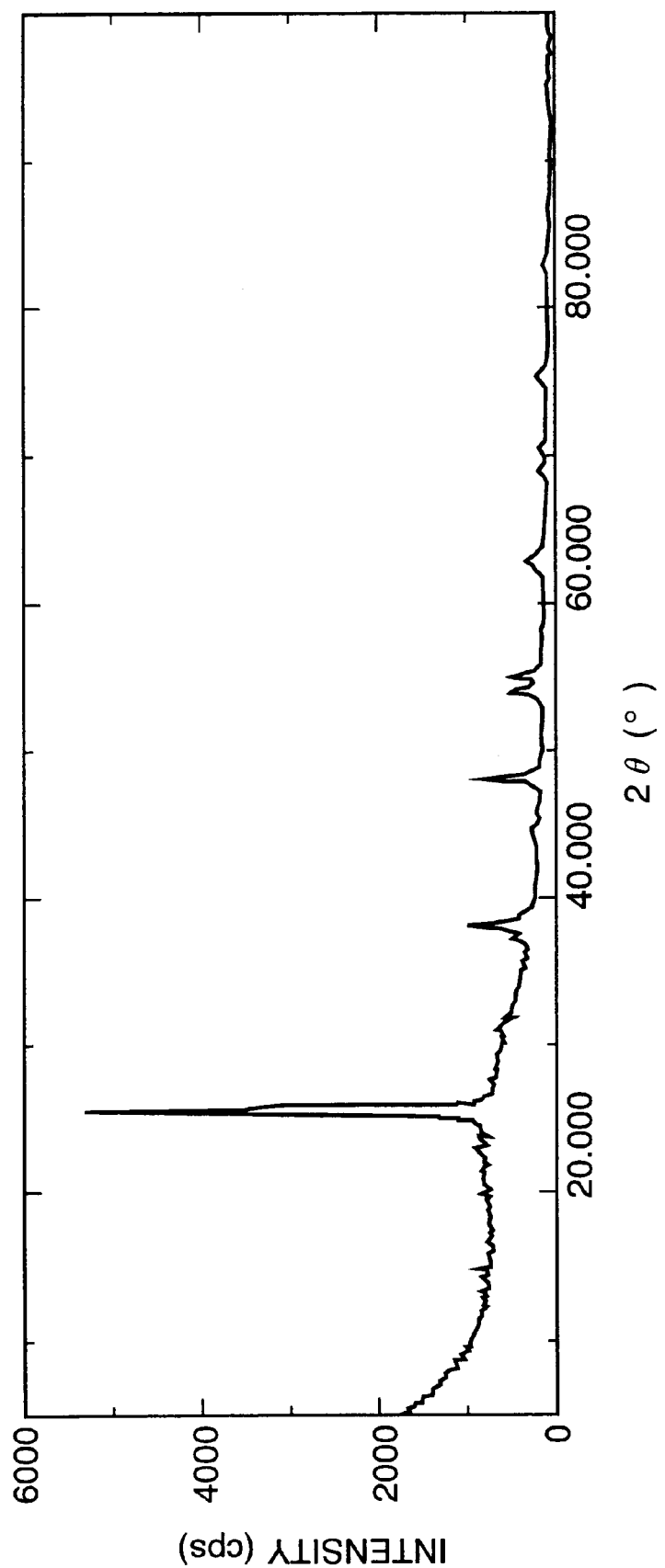
FIG. 5 is a X-ray diffraction spectrum of the thin film of titanium oxide.
Figures 6A, 6B:
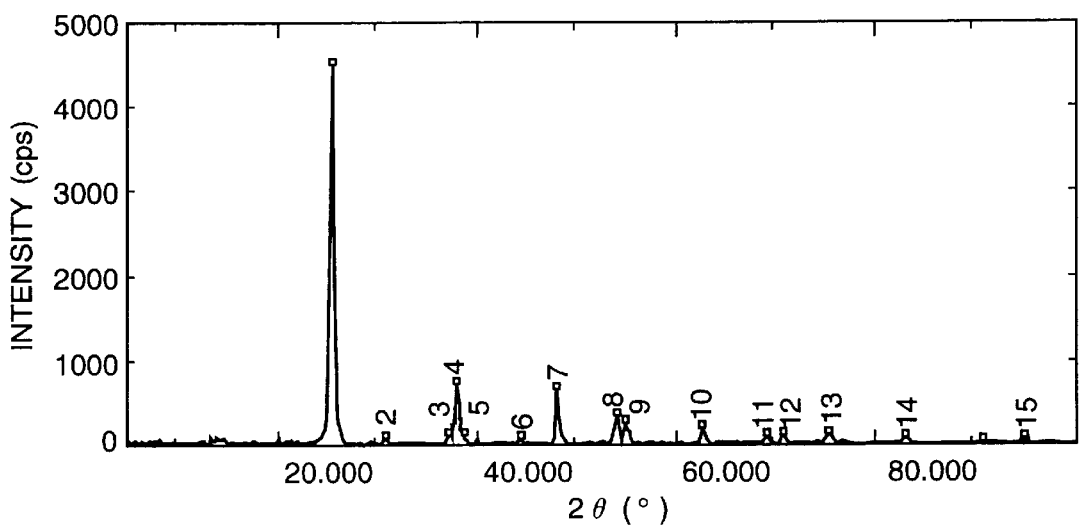
FIG. 6(A) and 6(B) are a processed spectrum of the spectrum shown in FIG. 5 and a table of the analyzed results of the processed spectrum, respectively.

In an example of identifying the crystal structure of the film formed on the glass substrate, it was determined by a laser Raman spectroscopic analysis that the crystal structure of the thin film of titanium dioxide having a thickness of 530 nm (confirmed by a sectional image obtained by using a scanning electron microscope) had the structure of a 100% anatase-type crystal. As shown by the Raman spectrum of the crystal structure of the film, as seen in FIG. 4, the main peak positions (640, 518, 396, and 197 cm$^{-1}$) in the obtained spectrum coincide with the peak positions (640, 515, 400, and 197) in the spectrum of a single crystal anatase-type titanium dioxide, which is reported in a paper "Proc. Roy. Soc. (London) A, vol. 307, p.407 (1968), by I. R. Beattie, and T. R. Gilson". It was determined by an X-ray diffraction pattern that the bulk crystal structure of a sample of the film formed by the above-mentioned processing method has the structure of a 100% anatase-type crystal. From the peak positions of the intensity pair 2θ spectrum shown in FIG. 5 and the analysis results of the peaks shown in FIGS. 6(A) and 6(B), the peaks peculiar to the anatase-type crystal structure, that is, peaks at the intensity pair 2θ positions of 25.35, 37.9, 48.15, and 53.95, were observed. The size of a crystallite in the film sample was analyzed by the X-ray diffraction method and was determined to be 34.6 nm.

The light transmittance of the film formed by the above-mentioned method was measured by using a light measurement apparatus having a light source in the form of a fluorescent lamp, which radiates light having a light spectrum in the wave length range 290 nm–750 nm. In the measurement, the light was irradiated on one surface of a test piece, and the light passing through the test piece was detected from the opposite side. The test piece was composed such that a thin film of titanium dioxide was formed on each of the surfaces of a glass substrate. Therefore, two thin films of titanium dioxide, each thin film having a thickness of 530 nm, sandwiched the glass substrate. The measurement results showed that 98.8%–99.9% of the irradiated light was able to pass through each thin film, and the intensity of the irradiated light was scarcely decreased by the thin films of titanium dioxide. The above-mentioned value for one thin film having a thickness of 530 nm was calculated, based on the measured light transmittance of the test piece composed of a glass substrate and two thin films of titanium dioxide sandwiching the glass substrate and the measured light transmittance of only the glass substrate. The measured light transmittance of the thin film indicated a high value, independently of the light energy intensity irradiated on the film. The light transmittance value of 99.9% was obtained under the irradiation condition in which light having a light energy intensity (22.7 mW/cm$^2$) at an outside surface of the fluorescent lamp was irradiated on the test piece, and the light irradiation condition was almost the same as the condition obtained in the case where a thin film of titanium dioxide is formed on an outside surface of a fluorescent lamp.

Figure 7:
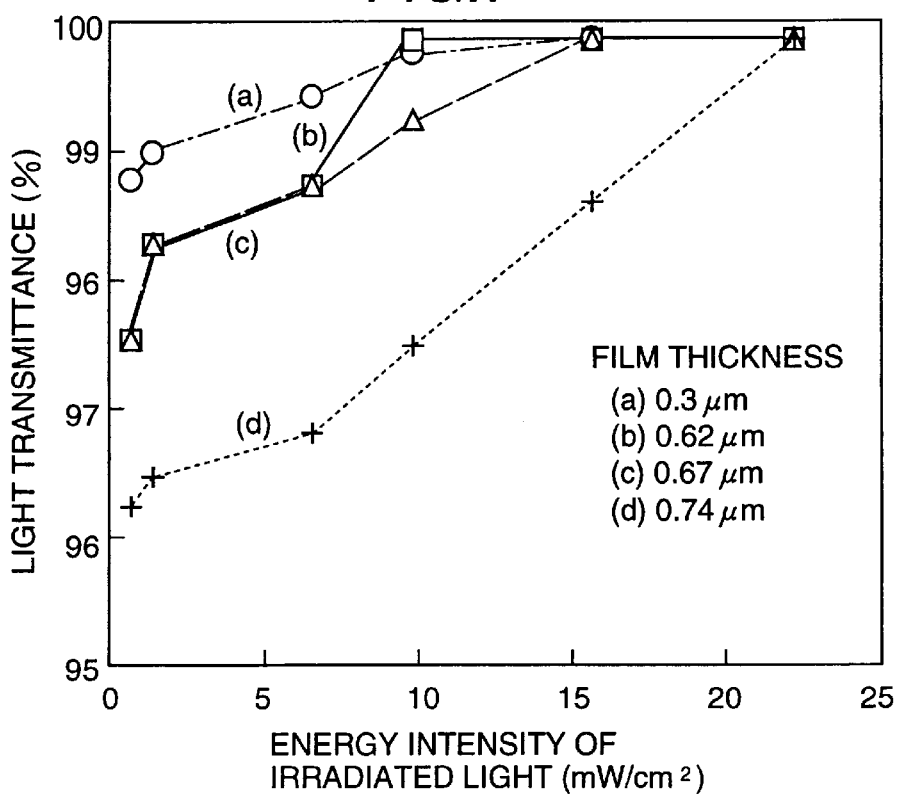
FIG. 7 is a graph showing the light transmittance of the thin film of titanium oxide applied on a glass substrate.

The light transmittance value of 98.8% was obtained under irradiation condition in which the light having a light energy intensity 0.69 mW/cm$^2$ at a position remote from an outside surface of the fluorescent lamp was irradiated on the test piece. Both of the obtained light transmittance values were high. Therefore, it was shown that the light transmittance of the thin film of titanium dioxide is sufficiently high at least within the light energy intensity range of 0.69–22,7 mW/cm$^2$. The relation between the light transmittance and the light energy intensity is shown in FIG. 7. In the figure, the effects of the thickness on the light transmittance are also shown. Although the light transmittance decreases as the thickness of the film increases from 530 nm (0.53 μm) to 740 nm (0.74 μm), the film has a high transmittance value of 96.3% even under the conditions of the 740 nm thickness and a 0.69 mW/cm$^2$ irradiated light energy intensity.

Figure 8:
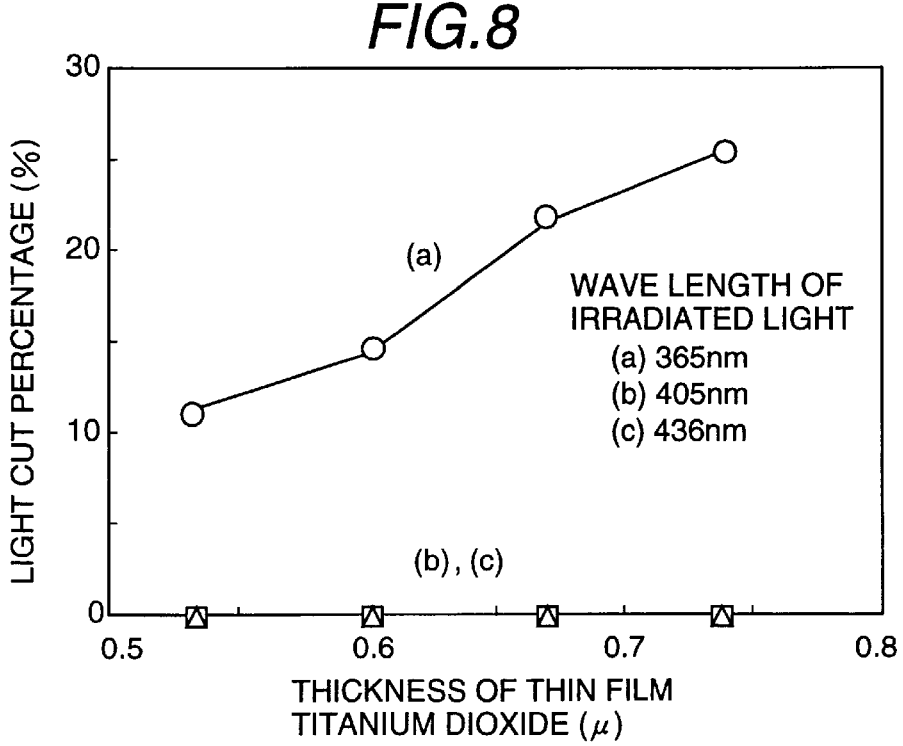
FIG. 8 is a graph showing the ultraviolet cut percentage of the thin film of titanium oxide applied on a glass substrate.

A thin film of titanium dioxide shows double effects of absorbing and cutting ultraviolet rays of less than 400 nm wave length corresponding to the band gap of the titanium dioxide, and of being excited by the absorbed ultraviolet light. The measurement results of the light cut percentage for various wave lengths included in the light at a surface of a fluorescent lamp are shown in FIG. 8. In the measurement, the above-mentioned test piece was used. It is shown by curve (a) in FIG. 8 that the light having a 365 nm wave length corresponding to the energy higher than band gap is absorbed. Furthermore, it is also shown by curves (b) and (c) that respective light having a wave length of 405 nm and a wave length of 436 nm, i.e. more than 400 nm, and outside the ultraviolet range, are not absorbed. The above-mentioned results show features peculiar to titanium dioxide. As to the light cut percentage (ultraviolet cut percentage) relating to the light having a 365 nm wave length, the light cut percentages are 11% and 25% at the film thickness of 0.53 μm and the film thickness of 0.74 μm, respectively, and the light cut percentages increase as the film thickness increases. Each light cut percentage shown in FIG. 8 is a half of the value including the cutting effects caused by the two films formed on both surfaces of the glass substrate. Therefore, the light cut percentage at the film thickness of 0.74 μm is 50% if the cutting effects caused by the two films are added.

[Embodiment 2]

In the following, results of testing decontamination deodorization, and bactericidal and fungicidal effects caused by a thin film of titanium dioxide will be summarized.

Figure 9:
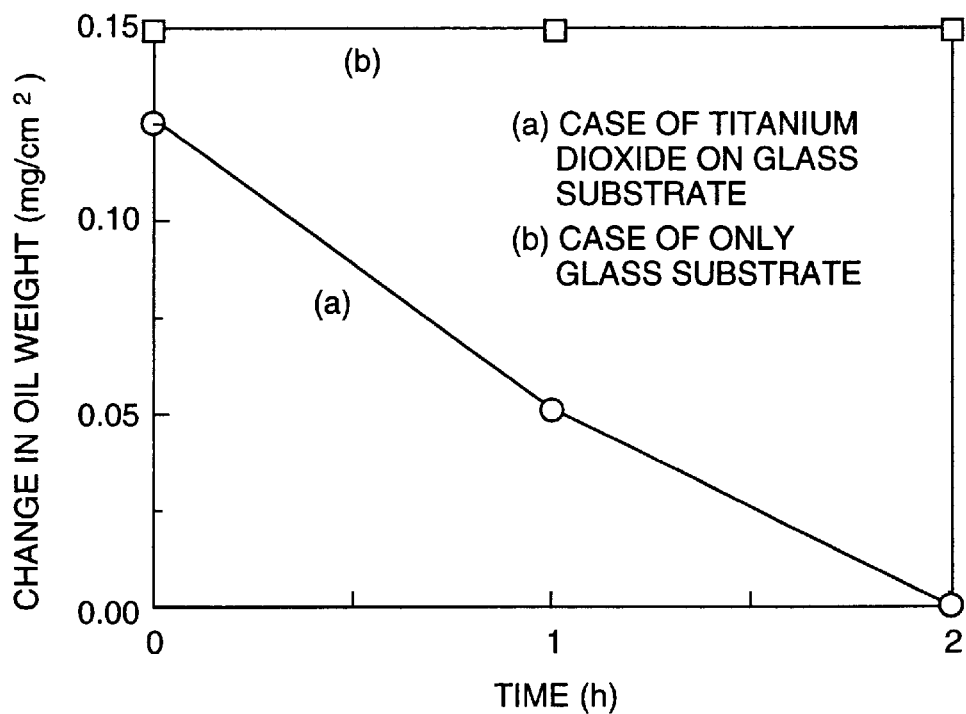
FIG. 9 is a graph showing the decontamination effects (decomposition of salad oil) of the thin film of titanium oxide applied on a glass substrate.

After salad oil is applied on a surface of a thin film of titanium dioxide (having a thickness of 0.53 μm) formed on a glass substrate, the initial weight of the applied oil and decreasing changes in the oil irradiated by light radiated from a fluorescent lamp were measured. The results of the measurement in the air environment are shown in FIG. 9. At two hours after the start of reaction (irradiation of the light), the applied oil was decomposed by oxidation, and vanished. A self-cleaning effect of the thin film of titanium dioxide was also confirmed. That is, after the oil was decomposed, decomposed products did not exist on the surface, and the surface of the thin film returned to the original clean surface. It is inferred that, in the decomposition process caused by the titanium dioxide, carbon-carbon bonds of the salad oil made of long-chain hydrocarbon were cut one after another and oxidized, and finally converted to carbon dioxide and water. As mentioned above, in the test on the titanium dioxide sample, it was shown that the thin film of titanium dioxide can decompose oil. Generally, the accumulation of dust occurs by adsorption of oil substances in the air to a surface of an object, and this is followed by adsorption of dust to the sticky surface. Therefore, the decomposition of oil is effective in preventing the accumulation of dust on a surface of an object.

Figure 10:
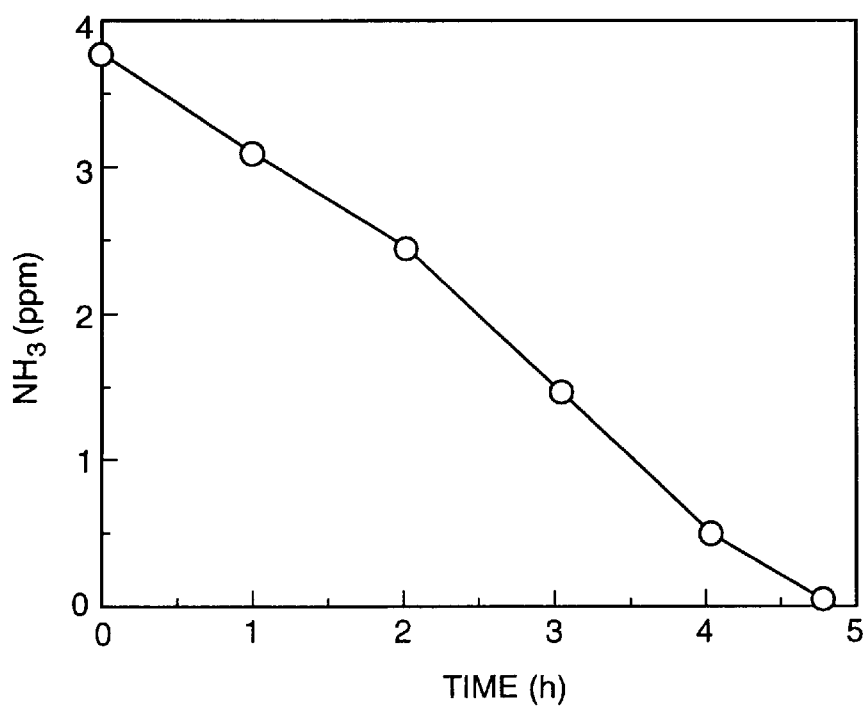
FIG. 10 is a graph showing the deodorization effects (decomposition of ammonia) of the thin film of titanium oxide applied on a glass substrate.

The deodorization effect of the thin film photocatalyst was measured by using the test piece used in the above-mentioned test. The measurement was carried out in a test system involving a closed-circulation system. In the test system an inert material was used to make an inside wall of a reactor unable to adsorb a very small quantity of substances to the wall surface, and gas contained in the reactor was stirred by a bellows circulation pump, in which oil is not used in order to avoid contamination by the oil. A sample holder for holding the test piece was provided at the central part of the reactor, and light was irradiated on the test piece through a special light-transmissive window from the outside. The gas contained in the reactor was lead to an atmospheric gas measurement device (apparatus for sending atmospheric gas to a gas chromatography mass spectrometer system) via a sampling valve, and the concentration time-changes of harmful substances in the gas contained inside the reactor were traced. In FIG. 10, the measurement results in decomposition reactions of ammonia were shown when light from a fluorescent lamp was irradiated on the test piece. The total light energy intensity of the irradiated light at a surface of the test piece was 1.5 mW/cm$^2$, and the light energy intensity of a light component having a 365 nm wave length in the irradiated light was 20 μW/cm$^2$. From the measurement results, it was confirmed that the decomposition of ammonia was completed in five hours. In the decomposition reactions of ammonia, it is inferred that the ammonia was finally decomposed into nitrogen and water. The same test piece which was turned upward, was immersed below and in the vicinity of a surface an ammonia aqueous solution of pH 9 contained in the reactor, and light from a fluorescent lamp was irradiated on the test piece from the front side of the test piece where the thin film photocatalyst was coated. After the irradiation of the light, the pH value of the aqueous solution was observed to be a neutral value of 7. The results shows that the ammonia was completely decomposed.

Figure 11:
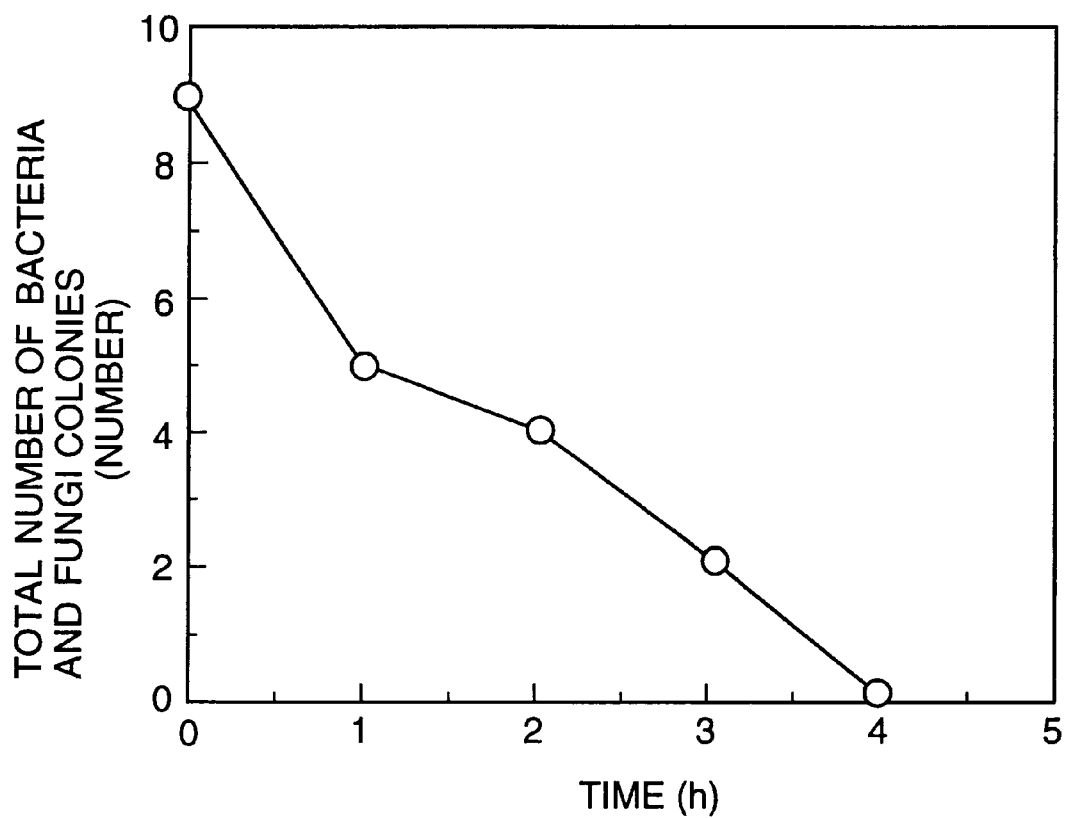
FIG. 11 is a graph showing the sterilization effects (sterilization of bacteria and fungi in the air) of the thin film of titanium oxide applied on a glass substrate.

Moreover, the bactericidal and fungicidal activity of the thin film photocatalyst was tested by using the same test piece and the same test system. The bacteria and fungi in the test were those living in the air of a room. The same light source in the form of a fluorescent lamp was used, and the total light energy intensity of light at the surface of the test piece and the light energy intensity of the light of 365 nm wave length were the same as those of the light used in the above-mentioned test. The bactericidal and fungicidal activity was measured by a method in which the room air was enclosed in the test system, and after the photocatalytic reactions in the test system continued for a definite time, the bacteria and fungi in the enclosed air were sampled for a definite time. The sampling was repeated periodically. The sampling was carried out by a by-pass method in which a new sampler was provided in the circulation system in each time. A culture fluid was fed into the sampler, and after the bacteria and fungi in the sampler were cultivated for 48 hours in an incubator in which the temperature was kept at 30° C., the number of fungus colonies was counted. The results of the test are shown in FIG. 11. The number of colonies counted at the start of the test was 9, and the number of colonies counted at 4 hours after the start time was 0 which means that all detectable bacteria and fungi contained in the enclosed air died after 4 hours from the start of the test. From the results of the test, it was confirmed that the thin film photocatalyst has a bactericidal and fungicidal effect. Furthermore, the same test piece which was turned upward, was immersed below and in the vicinity of the surface of water containing mold bacteria and fungi, and light of a fluorescent lamp was irradiated on the test piece. It was confirmed that the mold bacteria and fungi decreased remarkably.

[Embodiment 3]

In the following, a method of producing a thin film of iron oxide and the results of evaluating the physical property of the thin film will be explained.

A sol solution was made by mixing iron nitrate, ethylene glycol and nitric acid. After the sol solution was coated on a surface of a glass substrate of the same composition as that of a soda-lime glass tube typically used in a fluorescent lamp, a thin film of iron oxide was formed by a sol-gel processing method in which the coated sol solution was dried as the temperature was increased from 100° C., and baked at 600° C. By the above-mentioned processing, a colored and very light-transmissive thin film of iron oxide was formed.

Figure 12:
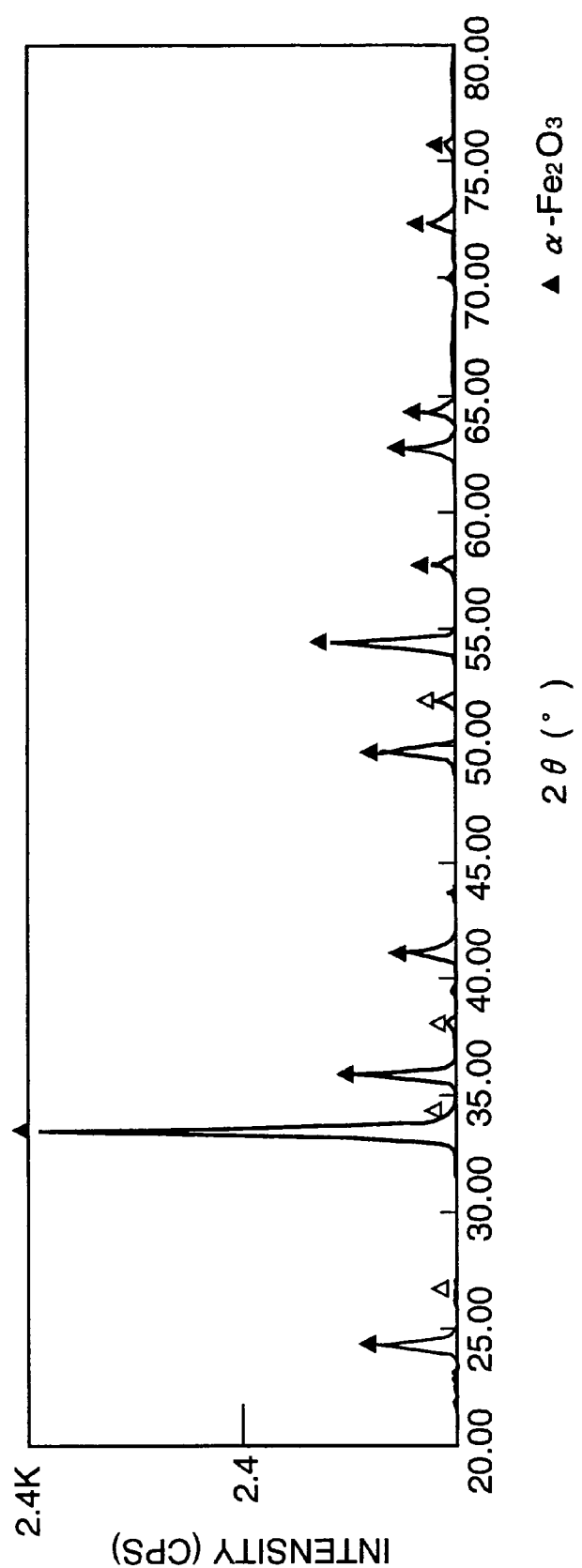
FIG. 12 is a processed X-ray diffraction spectrum of the thin film of iron oxide applied on a glass substrate.
Figure 13:
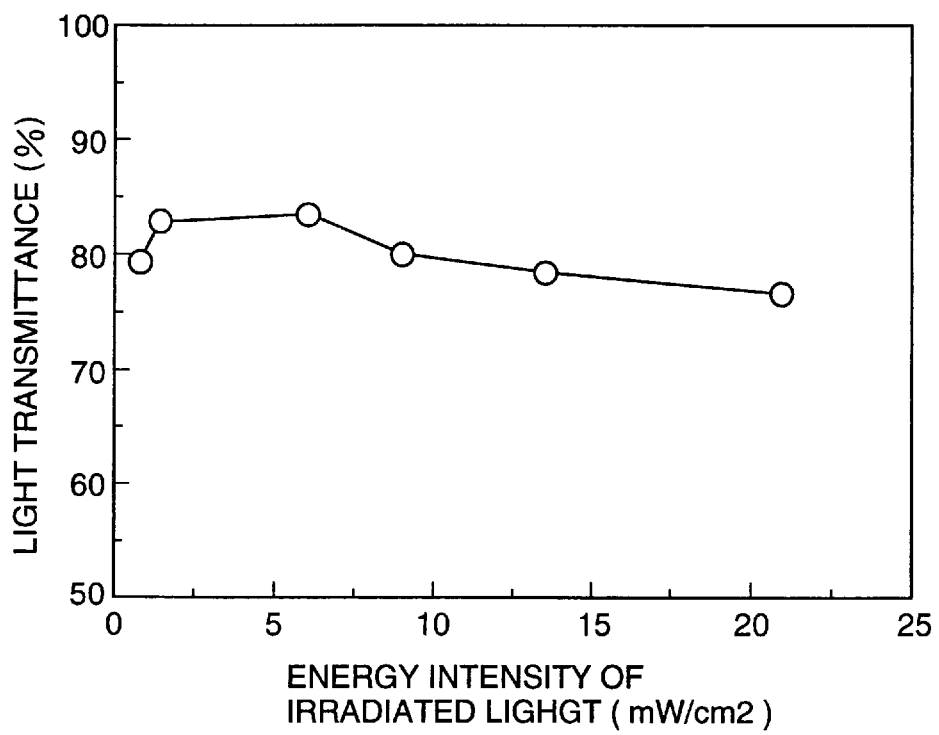
FIG. 13 is a graph showing the light transmittance of a thin film of iron oxide applied on a glass substrate.

It was confirmed by examining an X-ray diffraction pattern of the iron oxide that the formed light-transmissive iron oxide having a thickness of 50 nm (confirmed from a sectional image obtained by using a scanning electron microscope) is alpha iron oxide ($\alpha$-$Fe_2O_3$). As shown by a spectrum of intensity pairs 2θ in FIG. 12, the spectrum has four peaks particular to alpha iron oxide, that is, peaks at 2θ values of 51.9, 38.1, 34.0 and 33.4. The thin film of iron oxide is able to transmit light in a wave length range of 290–1200 nm, similar to the thin film of titanium dioxide. In the light transmittance measurement of the thin film iron oxide, a light energy intensity measurement apparatus was used, in which a fluorescent lamp radiating light in a wave length range of 290 nm–750 nm, was provided as a light source. From the measurement results, it was confirmed that the thin film $\alpha$-$Fe_2O_3$ had a more than 75% light transmittance, which was almost independent of the energy intensity of the irradiated light, as shown in FIG. 13. In the case of the irradiated light energy intensity of 20.8 mW/cm$^2$ at an outside surface of the fluorescent lamp, the thin film of iron oxide with a thickness of 50 nm had a light transmittance of 75.8%. In measuring the light transmittance of the thin film while increasing the thickness of the thin film to 90 nm and 260 nm, the light transmittance decreased to 64.8% and 38.9%.

Figure 14:
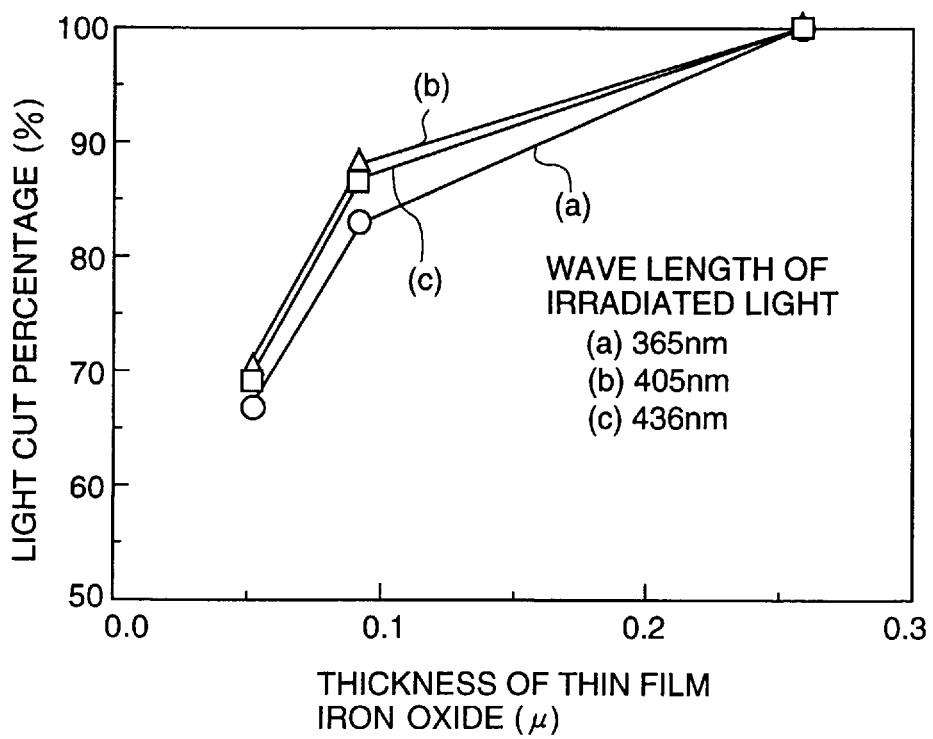
FIG. 14 is a graph showing the visible light cut percentage of the thin film of iron oxide applied on a glass substrate.

The thin film of iron oxide has the physical property of absorbing light of less than 540 nm wave length corresponding to its band gap. As shown in FIG. 14, the thin film of iron oxide absorbs visible light of 405 nm and 436 nm wave lengths, besides ultraviolet light of a 365 nm wave length, and is excited by the absorbed light. The iron oxide is different from the titanium in the above-mentioned light absorption property of the visible light. The light cut percentage of a 365 nm ultraviolet light increased to 66.7%, 83.8% and 100%, as the thickness of the thin film increased to 50 nm, 90 nm and 260 nm. The light cut percentages of a 405 nm visible light, corresponding to the above-mentioned thickness values, were 69.2%, 88.5% and 100%, respectively. The light cut percentages of a 436 nm visible light, corresponding to the above-mentioned thickness values, were 69.2%, 88.5% and 100%, respectively.

[Embodiment 4]

In the following, a method of producing a thin film photocatalyst coated on a glass tube and results of evaluating the physical property of the coated thin film will be explained.

Figure 15:
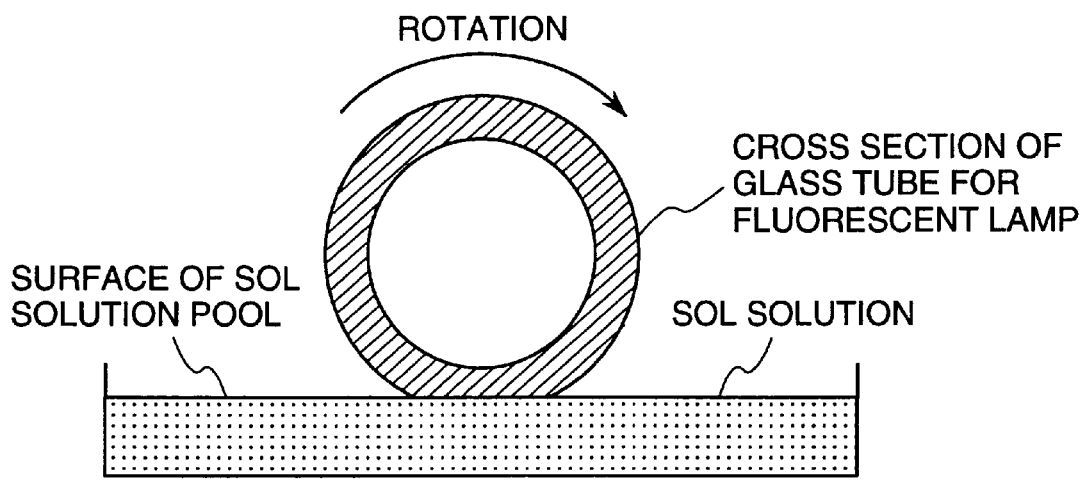
FIG. 15 a side cross-sectional view showing the thin film photocatalyst forming process using a contact rotation method.
Figure 16:
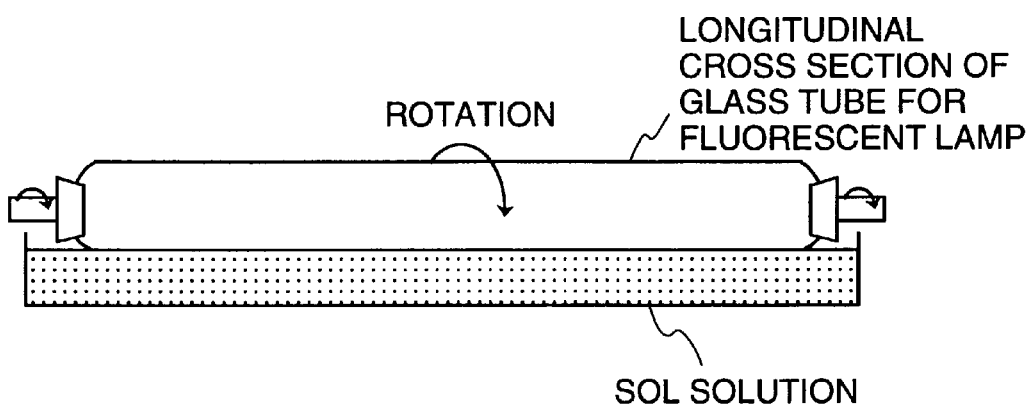
FIG. 16 a longitudinal cross-sectional view showing the thin film photocatalyst forming process by using a contact rotating method.
Figure 17:
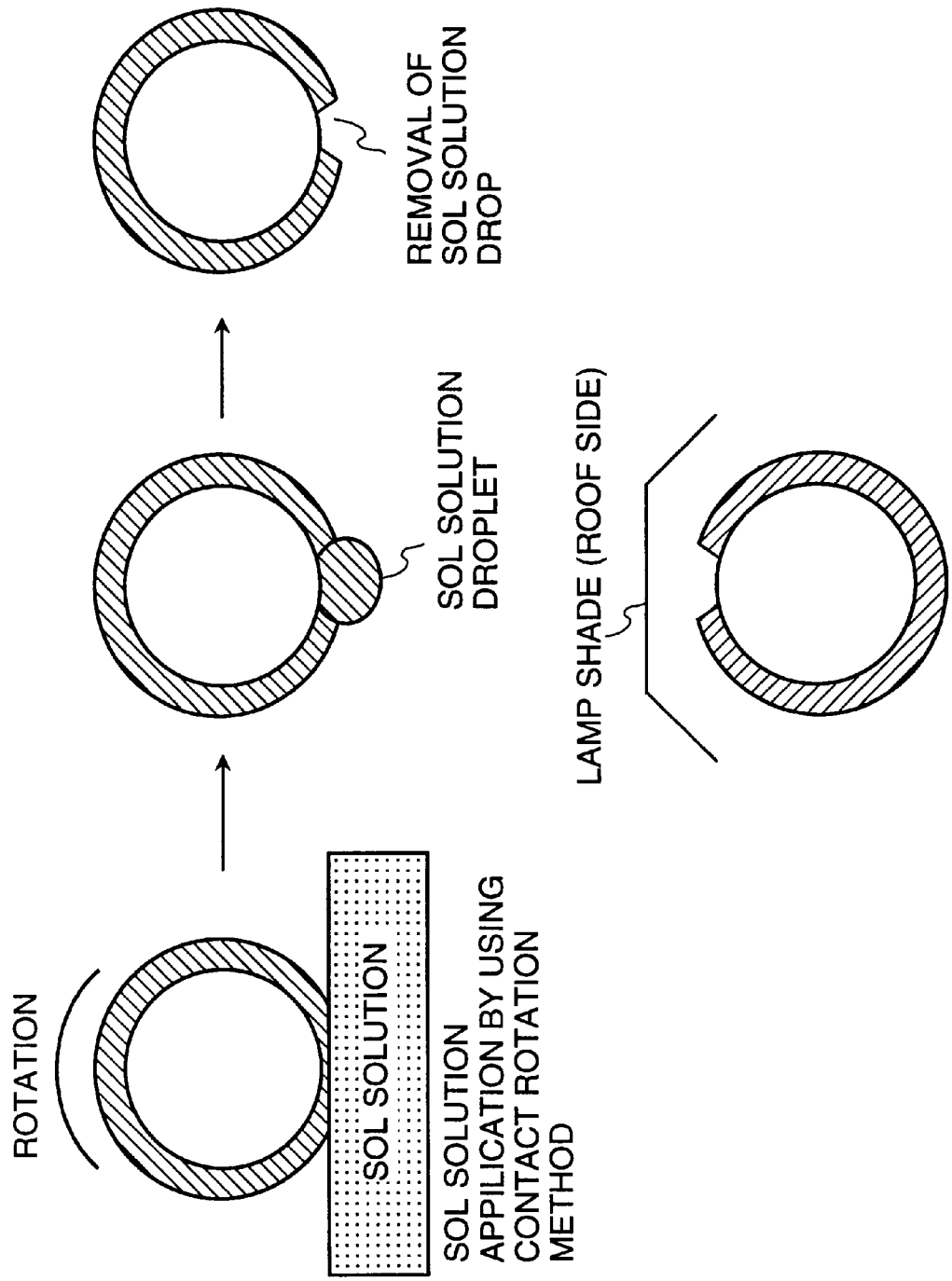
FIG. 17 is a diagram for explaining the processing states of the thin film photocatalyst formed by using the contact rotating method.
Figure 18:
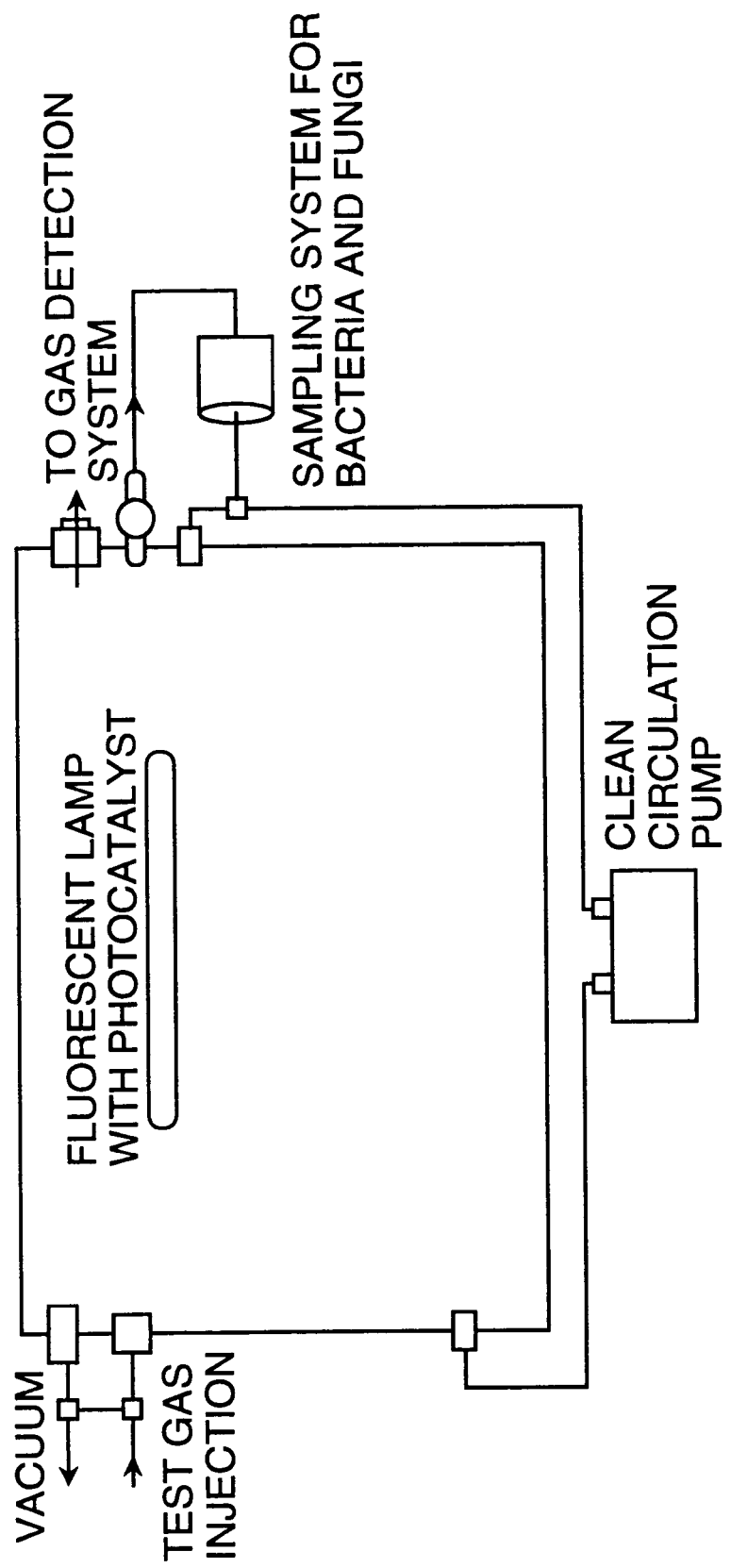
FIG. 18 is a schematic diagram of a reaction testing apparatus for examining the bactericidal and fungicidal activity and the deodorization effect achieved by a fluorescent lamp having a photocatalyst according to the present invention.

An outside surface of a soda-lime glass tube of the type used for a fluorescent lamp was horizontally held in contact with a surface of the same sol solution as the solution used in the embodiment 1, which was contained in a vessel, as shown in FIG. 15 and FIG. 16. The glass tube, whose outside surface was in contact with a surface of a pool of the sol solution, was rotated at a constant speed through one rotation, and the rotation of the tube was then stopped. The outside surface of the glass tube was then lifted from the surface of the sol solution pool. On lifting the glass tube from the surface of the sol solution pool, droplets of the solution dripping from the adhered sol solution on the glass tube were formed, and the droplets caused a non-uniformity in the thickness of the coated sol solution. In order to remove or reduce the droplets, a part where the droplets are formed, was brought into contact with water or an alcohol aqueous solution, or the drops are wiped off with water or an alcohol aqueous solution, at an adequate timing. Although the photocatalyst is not formed, or the thickness of the photocatalyst is reduced, at the part of the glass tube from which the drops are wiped-off or removed, it is possible to exclude the influences of the problem area where no-photocatalyst or a reduction in the thickness of the photocatalyst occurs, by positioning the problem area of the glass tube at the side pacing a lamp shade, and consequently positioning the dominant part coated with the thin film photocatalyst, other than the problem area, at the side facing away from the lamp shade, so as to sufficiently contact the room air. After causing the sol solution to adhere to the surface of the glass tube, the adhered sol solution was baked at 500° C. By the above-mentioned sol-gel processing method, condensation polymerization between hydroxyl groups of titanium hydroxide and hydroxyl groups existing at the surface of the glass substrate proceeded, and strong chemical bonding of titanium dioxide and silicon oxide, which is a dominant component of soda-lime glass, also proceeded. As a result, a high light transmissive and transparent thin film of titanium dioxide was obtained on the outside surface of the glass tube.

The thickness of the thin film of titanium dioxide formed on the outside surface of the glass tube used for the fluorescent lamp was measured by using a sectional image of the thin film and the glass obtained by a scanning electron microscope, and the thickness was found to be 370 nm, ±10 nm which indicates a highly uniform thickness. It was determined by analyzing a measured X-ray diffraction pattern that the crystal structure of the thin film was 100% anatase-type titanium dioxide, similar to the measurement results in the embodiment 1. The d value at the intensity pair $2\theta$ of 25.35 was 3.5105, characteristic of anatase-type titanium dioxide.

The light transmittance of the above-mentioned anatase type titanium dioxide was measured and found to be 96.3% to light having a spectrum of a 200–1200 nm wave length range, and 97.6% to light having a spectrum of a 200–700 nm wave length range. In irradiating ultraviolet light of a 365 nm wave length (UVA:near ultraviolet which has a 325 nm–388 nm wave length range, mainly includes ultraviolet of a 365 nm wave length) corresponding to an energy higher than the band gap of the titanium dioxide of the thin film, the absorption of about 20% of the ultraviolet was observed. It was confirmed that the absorption of light did not occur in the case of irradiation with light having a wave length in a range of 405 nm–436 nm, i.e. outside the ultraviolet range including light of a wave length shorter than 400 nm.

[Embodiment 5]

In the following, the test results of the bactericidal and fungicidal activity, the deodorization effect and the contamination preventing effect of a fluorescent lamp with the thin film photocatalyst will be explained.

Figure 19:
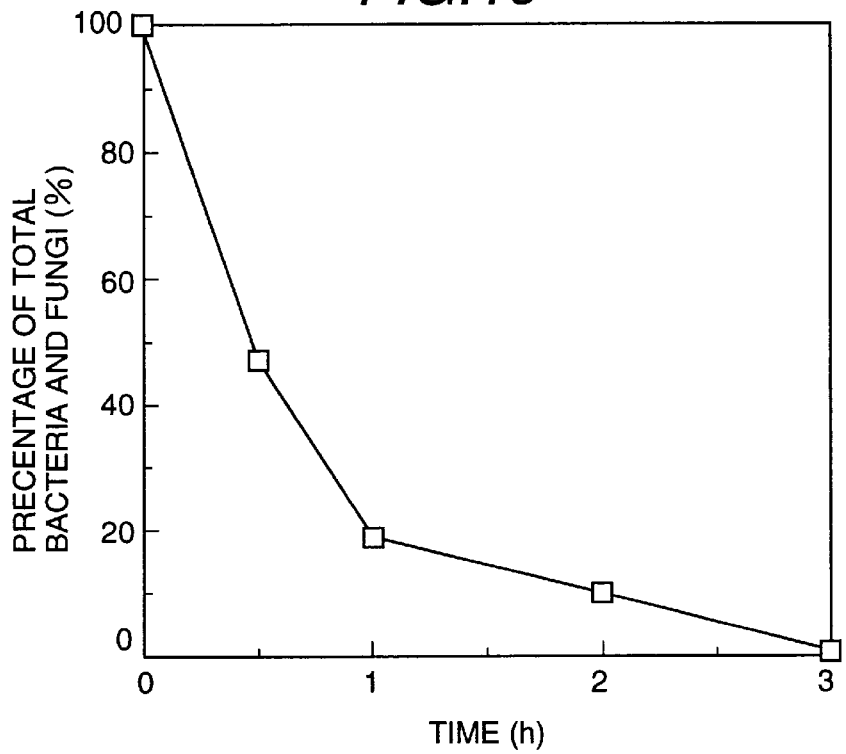
FIG. 19 is a graph showing the relation between the percentage survival of total bacteria and fungi, and the lapse achieved by time, which indicates the sterilization effects of the fluorescent lamp having a photocatalyst according to the present invention.

The bactericidal and fungicidal activity, with respect to bacteria and fungi in the air of a room, of a fluorescent lamp with a thin film photocatalyst formed by the above-mentioned process, was tested by using a reaction testing apparatus in which a fluorescent lamp with the film photocatalyst was provided and turned on, and a part of the air including bacteria and fungi was enclosed. The reaction testing apparatus was a closed gas circulation system. The activity was confirmed by a method in which, after the photocatalytic reactions of the enclosed air were continued for a definite time, the bacteria and fungi included in the enclosed air were sampled for a definite time. The sampling was carried out by a by-pass method in which a new sampler was provided in the circulation system in each sampling period. A culture fluid was fed into the samples, and after the sampler were cultivated for 72 hours in an incubator in which the temperature was kept at 30° C, the number of colonies was counted. As shown in FIG. 19, indicating test results, the surviving percentage decreased to 0 in about 3 hours after the light irradiation on the thin film photocatalyst was produced by switching on the fluorescent lamp with the photocatalyst coating. Therefore, the bactericidal and fungicidal effect caused by the fluorescent lamp with the thin film photocatalyst was clearly shown. It is inferred that the light radiated from the fluorescent lamp passed through the glass tube and generated various kinds of active species at an outside surface of the thin film photocatalyst as the light was passed through the thin film, and the generated active species sterilized the bacteria and fungi in the air.

Figure 20:
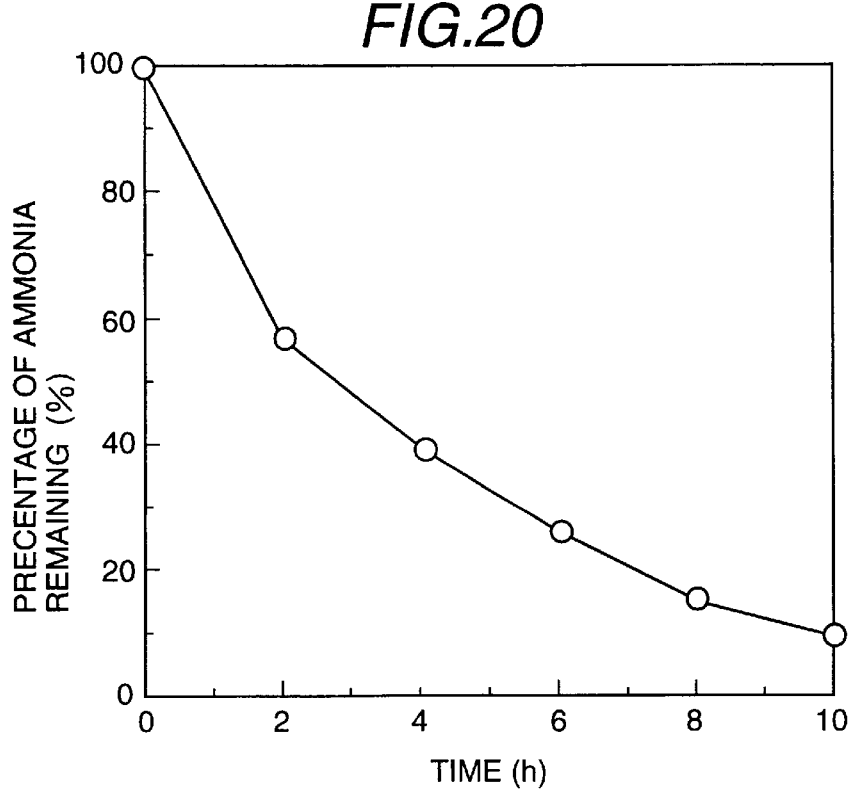
FIG. 20 is a graph showing results of an experiment for testing the decomposition of ammonia, which indicates the deodorization effects achieved by the fluorescent lamp having a photocatalyst according to the present invention.

Furthermore, the deodorization effect of a fluorescent lamp with the thin film photocatalyst was confirmed by using the above-mentioned reaction testing apparatus. At first, after the air contained in the testing apparatus was exhausted and the testing apparatus was evacuated, then air containing ammonia in an amount of 10 ppm was fed into the testing apparatus. Next, the concentration of ammonia in the apparatus was measured by a gas detection system at a predetermined sampling period under an air recirculating condition, while the fluorescent lamp with the thin film photocatalyst was kept in a turned-on state. As shown in FIG. 20, indicating the test results, the remaining percentage of ammonia decreased to 10% in about 10 hours after starting the test, which clearly shows the decomposition effect of ammonia caused by the fluorescent lamp with the thin film photocatalyst. Although there are various possible mechanisms to decompose ammonia, in the above-mentioned ammonia decomposition, it is inferred that the ammonia was decomposed to nitrogen and water by oxidizing decomposition reactions caused by reactions between the ammonia and active oxygen.

Moreover, the contamination preventing effect of a fluorescent lamp with the thin film photocatalyst was tested. After salad oil was applied on a surface of a thin film of titanium dioxide (having a thickness of 530 nm) formed on a glass substrate of the same composition as that of a soda-lime glass tube typically used for a fluorescent lamp, the initial weight of the applied oil and decreasing changes of the oil irradiated by light radiated from a fluorescent lamp were measured. Similar results to ones which were shown in FIG. 9 were obtained, and at two hours after the start of reaction (irradiation of the light), the applied oil was decomposed by oxidation and vanished. A self-cleaning effect of the thin film titanium dioxide was also confirmed. That is, after the applied oil was decomposed, decomposed products did not exist on the surface, and the surface of the thin film returned to its original clean state. It is inferred that, in the decomposition process caused by the titanium dioxide, carbon-carbon bonds of the salad oil made of long-chain hydrocarbon were cut one after another and oxidized, and finally converted to carbon dioxide and water. As mentioned above, from the results of the test to the titanium dioxide sample, it is shown that the thin film titanium dioxide can decompose oil. Generally, the accumulation of dust occurs by adsorption of oil substances in the air onto a surface, and this is followed by adsorption of dust on the sticky surface. Therefore, the decomposition of oil is effective in preventing the accumulation of dust on the surface.

[Embodiment 6]

In the following, a method of producing a thin film of iron oxide and the results of evaluating the physical property of the thin film of iron oxide formed by the method will be explained.

At first, a sol solution was made by mixing iron nitrate, ethylene glycol and nitric acid. After the sol solution was coated on an outside surface of a glass tube of the type typically used in a fluorescent lamp, a thin film iron oxide was formed by the contact rotating method explained in the embodiment 4, as shown in FIG. 15 and FIG. 16, in which the coated sol solution is dried as the temperature is increased from 100° C. and baked at 600° C. By the above-mentioned processing, a colored and considerably light-transmissive thin film of iron oxide was formed. It was confirmed by examining an X-ray diffraction pattern of the iron oxide that the formed light-transmissive iron oxide with a thickness of 50 nm (confirmed from a sectional image obtained with a scanning electron microscope) was alpha iron oxide ($\alpha$-$Fe_2O_3$). In a spectrum of the intensity pairs 2$\theta$ of the thin film iron oxide, the spectrum had four peaks particular to $\alpha$-iron oxide, that is, four peaks at 2$\theta$ values of 51.9, 38.1, 34.0 and 33.4. It was confirmed that the thin film can transmit light in a wave length range of 200 nm–1200 nm, and also 70% of the light in a wave length range of 200 nm–700 nm.

The thin film of iron oxide has the physical property of absorbing light of less than 540 nm wave length corresponding to its band gap. The thin film of iron oxide absorbs visible light of 405 nm and 436 nm wave lengths, besides ultraviolet of a 365 nm wave length, and is excited by the absorbed light. The iron oxide is different from the titanium in the above-mentioned visible light absorbing property. The light cut percentages of light of wave lengths 365 nm, 405 nm and 436 nm were 66.7%, 69.2% and 69.2%, respectively.

What is claimed is:

1. A fluorescent lamp including a light transmissive glass tube, a thin film fluorescent substance applied on an inside wall of the glass tube, and a gas enclosed in said glass tube, said fluorescent lamp comprising:

a light transmissive and transparent thin film photocatalyst, made of one of titanium oxide having an anatase-type crystal structure and iron oxide having an alpha crystal structure, applied on an outside surface of said glass tube.

2. A fluorescent lamp including a light transmissive glass tube, a thin film fluorescent substance applied on an inside wall of the glass tube, bases and pins provided at both ends of said glass tube, and mercury and buffer gas enclosed in said glass tube, said fluorescent lamp comprising:

a light transmissive and transparent thin film photocatalyst, made of one of titanium oxide having an anatase-type crystal structure and iron oxide having an alpha crystal structure, applied on an outside surface of said glass lamp, wherein said thin film photocatalyst is formed so that electrons and holes generated within said thin film photocatalyst can rapidly move to a surface of said thin film photocatalyst.

3. A fluorescent lamp according to claim 1, wherein the thickness of said thin film photocatalyst made of titanium dioxide is within a range of 0.02–2 $\mu$m.

4. A fluorescent lamp according to claim 1, wherein the thickness of said thin film photocatalyst made of iron oxide is within a range of 0.01–0.1 $\mu$m.

5. A fluorescent lamp according to claim 1, wherein said thin film photocatalyst is formed so that electrons generated within said thin film photocatalyst by light irradiated on said film can rapidly move in a whole region within said film.

6. A fluorescent lamp according to claim 1, wherein said thin film photocatalyst is formed to a thin sheet in which crystallites made of one of titanium dioxide or iron oxide are two-dimensionally and continuously arranged.

7. A fluorescent lamp according to claim 1, wherein said thin film photocatalyst is formed by a sol-gel processing method.

8. A fluorescent lamp according to claim 1, wherein said thin film photocatalyst has a physical property of transmitting a light having a wave length in a range of 290 nm–1200 nm, and transmitting more than 90% of light with a wave length in a range of 290 nm–750 nm.

9. A method of producing a fluorescent lamp including a light transmissive glass tube, a thin film fluorescent substance applied on an inside wall of said glass tube, bases and pins provided at both ends of said glass tube, and mercury and buffer gas enclosed in said glass tube, said method comprising the steps of:

adhering a sol solution containing one of titanium dioxide and iron oxide to an outside surface of said glass tube, a fluorescent thin film being coated on an inside surface of said glass tube; and drying and baking said sol solution adhered to said outside surface of said glass tube in order to form a light transmissive and transparent thin film photocatalyst made of one of titanium oxide having an anatase-type crystal structure and iron oxide having an alpha crystal structure on said outside surface of said glass tube.

10. A method of producing a fluorescent lamp according to claim 9, wherein a sol solution, made of a mixture of titanium-alkoxide, acid and alcohol, is used as said sol solution for forming said thin film photocatalyst of titanium dioxide.

11. A method of producing a fluorescent lamp according to claim 9, wherein a sol solution, made of a mixture of iron compound, acid and alcohol, is used as said sol solution for forming said thin film photocatalyst of iron oxide.

12. A method of producing a fluorescent lamp according to claim 9, wherein the step of baking said sol solution adhered to said outside surface of said glass tube is carried out at a temperature of 450° C.–600° C. in the case of forming a thin film titanium oxide.

13. A method of producing a fluorescent lamp according to claim 9, wherein the step of baking said sol solution adhered to said outside surface of said glass tube is carried out at a temperature of 560° C.–770° C. in the case of forming a thin film iron oxide.

14. A method of producing a fluorescent lamp according to claim 9, wherein the step of adhering said sol solution to said outside surface of said glass tube is carried out by causing said outside surface of said glass tube to contact a surface in a pool of said sol solution and by rotating said glass tube in order to form a uniform and smooth sol solution thin film on said outside surface of said glass tube.

15. A method of producing a fluorescent lamp according to claim 9, wherein the step of adhering said sol solution includes a step of removing droplets of said sol solution, said droplets being formed when said rotating of said glass tube is stopped and said glass tube is lifted from said pool of sol solution.

16. Fluorescent lamp structure comprising at least two fluorescent lamps according to claim 1 neighboring each other.

17. A fluorescent lamp according to claim 1, wherein the light transmissive and transparent thin film photocatalyst is made of said iron oxide.

18. A fluorescent lamp according to claim 17, wherein the thickness of said thin film photocatalyst made of iron oxide is within a range of 0.01–0.1 $\mu$m.

19. A fluorescent lamp according to claim 1, wherein the light transmissive and transparent thin film photocatalyst is made of said titanium oxide.

20. A fluorescent lamp according to claim 19, wherein the thickness of said thin film photocatalyst made of titanium dioxide is within a range of 0.02–2 $\mu$m.

21. A fluorescent lamp including a light transmissive glass tube, a thin film fluorescent substance applied on an inside wall of said glass tube, bases and pins provided at both ends of said glass tube, and mercury and buffer gas enclosed in said glass tube, said fluorescent lamp being manufactured by a method comprising the steps of:

adhering a sol solution containing one of titanium dioxide and iron oxide to an outside surface of said glass tube, a fluorescent thin film being coated on an inside surface of said glass tube; and drying and baking said sol solution adhered to said outside surface of said glass tube in order to form a light transmissive and transparent thin film photocatalyst made of one of titanium oxide having an anatase-type crystal structure and iron oxide having an alpha crystal structure on said outside surface of said glass tube.

22. A fluorescent lamp according to claim 21, wherein said light transmissive and transparent thin film photocatalyst is made of said titanium oxide.

23. A fluorescent lamp according to claim 22, wherein a sol solution made of a mixture of titanium-alkoxide, acid and alcohol, is used as said sol solution for forming said thin film photocatalyst of titanium oxide.

24. A fluorescent lamp according to claim 23, wherein the steps of baking said sol solution adhered to said outside surface of said glass tube is carried out at a temperature of 450°–600° C.

25. A fluorescent lamp according to claim 21, wherein said light transmissive and transparent thin film photocatalyst is made of said iron oxide.

26. A fluorescent lamp according to claim 25, wherein a sol solution made of a mixture of iron compound, acid and alcohol, is used as said sol solution for forming said thin film photocatalyst of iron oxide.

27. A fluorescent lamp according to claim 26, wherein the step of baking said sol solution adhered to said outside surface of said glass tube is carried out at a temperature of 560°–770° C.

* * * * *